(12) United States Patent
Bärwinkel et al.

(10) Patent No.: US 9,510,738 B2
(45) Date of Patent: Dec. 6, 2016

(54) INSTRUMENT SYSTEM

(75) Inventors: Ronny Bärwinkel, Dormitz (DE);
Oliver Hornung, Fürth (DE);
Karl-Heinz Maier, Altdorf b. Nürnberg (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 131 days.

(21) Appl. No.: 13/885,183

(22) PCT Filed: Nov. 10, 2011

(86) PCT No.: PCT/EP2011/069794
§ 371 (c)(1),
(2), (4) Date: May 14, 2013

(87) PCT Pub. No.: WO2012/065895
PCT Pub. Date: May 24, 2012

(65) Prior Publication Data
US 2013/0245370 A1   Sep. 19, 2013

(30) Foreign Application Priority Data
Nov. 18, 2010   (DE) .................. 10 2010 044 106

(51) Int. Cl.
*A61B 17/32* (2006.01)
*A61B 1/018* (2006.01)
(Continued)

(52) U.S. Cl.
CPC ........... *A61B 1/018* (2013.01); *A61B 1/00149* (2013.01); *A61B 1/3132* (2013.01);
(Continued)

(58) Field of Classification Search
CPC ... A61B 1/018; A61B 1/3132; A61B 1/00149; A61B 17/3421; A61B 17/3201; A61B 17/00234; A61B 17/29; A61B 2017/2905; A61B 2017/2927; A61B 2017/3492; A61B 2017/003; A61B 2017/00323; A61B 2017/3443; A61B 2017/2908; A61B 2019/2242; A61B 19/2203
See application file for complete search history.

(56) References Cited

U.S. PATENT DOCUMENTS

| 4,863,430 A | 9/1989 | Clawson |
|---|---|---|
| 5,743,880 A | 4/1998 | Hlavka |
| (Continued) | | |

FOREIGN PATENT DOCUMENTS

| AU | 655323 B2 | 12/1994 |
|---|---|---|
| DE | 4002235 A1 | 8/1990 |
| (Continued) | | |

Primary Examiner — Ashley Fishback

(57) ABSTRACT

An instrument system is provided. The instrument system has an endoscopic instrument with a work head that is mounted on one end of a flexible support arm and can be inserted into a patient. The instrument system has a trocar that can be placed in the body surface of the patient and has a main body which can be fixed in position relative to the patient and which has a through-opening for the instrument, a guide body which, when the instrument is inserted, encloses and guides a longitudinal portion of the support arm with a guide channel in such a way that a spatial guiding direction of the support arm is defined at least thereon, with an adjustment element acting on the guide body and allowing a specific change of a relative position of the guiding direction with respect to the main body.

6 Claims, 3 Drawing Sheets

(51) Int. Cl.
*A61B 1/00* (2006.01)
*A61B 1/313* (2006.01)
*A61B 17/34* (2006.01)
A61B 17/00 (2006.01)
A61B 17/29 (2006.01)
A61B 17/3201 (2006.01)

(52) U.S. Cl.
CPC .......... *A61B 17/3421* (2013.01); *A61B 34/30* (2016.02); *A61B 34/71* (2016.02); *A61B 17/00234* (2013.01); *A61B 17/29* (2013.01); *A61B 17/3201* (2013.01); *A61B 2017/003* (2013.01); *A61B 2017/00323* (2013.01); *A61B 2017/2905* (2013.01); *A61B 2017/2908* (2013.01); *A61B 2017/2927* (2013.01); *A61B 2017/3443* (2013.01); *A61B 2017/3492* (2013.01)

(56) References Cited

U.S. PATENT DOCUMENTS

| | | | | |
|---|---|---|---|---|
| 5,899,914 A | * | 5/1999 | Zirps | A61B 17/1608 606/170 |
| 6,554,793 B1 | * | 4/2003 | Pauker et al. | 604/95.01 |
| 2007/0260273 A1 | | 11/2007 | Bakos | |

FOREIGN PATENT DOCUMENTS

| | | |
|---|---|---|
| DE | 102007010304 A1 | 9/2008 |
| EP | 2172156 A1 | 4/2010 |
| WO | WO 2010009070 A1 | 1/2010 |
| WO | WO 2010068004 A2 | 6/2010 |

* cited by examiner

INSTRUMENT SYSTEM

CROSS REFERENCE TO RELATED APPLICATIONS

This application is the US National Stage of International Application No. PCT/EP2011/069794 filed Nov. 10, 2011 and claims benefit thereof, the entire content of which is hereby incorporated herein by reference. The International Application claims priority to the German application No. 10 2010 044 106.6 DE filed Nov. 18, 2010, the entire contents of which is hereby incorporated herein by reference.

FIELD OF INVENTION

The invention relates to an instrument system.

BACKGROUND OF INVENTION

The invention relates to an instrument system for minimally-invasive surgery.

Minimally-invasive interventions are assuming an increasingly great importance in the field of clinical surgery. While just a few years ago relatively large areas of the site were opened up for small surgical interventions, to make it possible for the surgeon to navigate through natural landmarks, it can be observed that a plurality of these interventions are nowadays carried out by means of laparoscopy and optical support in the form of endoscopy. This trend is likely to continue, aided by the direct advantages of minimally-invasive interventions. Endoscopes, laparoscopes etc. are referred to below by the general term endoscopic instruments, which are generally brought by a trocar placed into the inside of the patient. Instruments and trocar together form an instrument system.

Tele-operated robotic assistance systems are also known as instrument systems in which the surgeon enters movements at a console. The movement entries are then transmitted, scaled via a suitable kinematics system, to the instruments located in the body of the patient. Trocars are also used as a rule for this purpose. In other words a robot arm carries an instrument, wherein the robot arm in its turn is remotely controlled by the surgeon. The said robot assistance systems are playing a decisive role in systems currently being developed for the market.

There are numerous possible solutions for the design of the kinematics of said assistance systems. The instruments used are generally rigid. Their movements are effected by a robot arm located outside the patient. Previously a disruptively large space requirement has been necessary for this.

Newer concepts are also conceivable, which counteract this disadvantage. In accordance with said concepts the instruments themselves are equipped with ever greater degrees of freedom of movement. Many movements of the instruments then take place within the patient's body. Such movements no longer have to be actuated by the robot assistance system outside the body. The work space required for the robot outside the body thus remains restricted. The majority of the operational movements are thus implemented by kinematics with multiple degrees of freedom within the site.

A challenge now arises with these approaches in realizing a plurality of degrees of freedom for instrument movement with a small instrument diameter, to enable the instrument to be placed with a suitable trocar diameter. Such a diameter lies for example in the range of less than 10 mm. It is conceivable for example to drive the axes of the instrument's degrees of freedom primarily by cable constructions instead of by an electrically operated actuator, so that the instrument remains a low-cost instrument. This is designed to provide a disposable concept.

Disadvantageously at least two cables must be fed through the instrument structure for each degree of freedom of movement, to enable two directions of movement to be realized for the particular applied force or applied torque. This already results, for an instrument of which the movements cover the six degrees of freedom of the space, in the use of twelve cables at the most unfavorable point. Even if the first of the six axes is driven directly outside the patient, a functionality is generally also required for a work head of the instrument, i.e. an end effector. E.g. if a gripper is to be able to be actuated at the instrument tip, two cables are then additionally required for this purpose. These too must be routed through the instrument structure.

FIG. 3 shows a schematic of a section of a conceivable instrument 20, containing a support arm 22 and a work head 24 attached to the end thereof. An actuator 38 on the work head 24 in the form of scissors is operated via control lines 32 in the form of cables. The actuation represents a first degree of freedom. The work head 24 is also able to be rotated in relation to the support arm 22, which represents a second degree of freedom or a second actuator 38. This too is operated via two control lines 32 in the form of cables. The support arm 22 has rigid arm segments 100 which are connected to each other via a joint 102. Thus the joint 102 also represents an actuator 38, which is likewise moved via two control lines 32 or cables respectively.

FIG. 3 shows the realization of an instrument of 8 mm in diameter, on the basis of which an idea of the complexity of such a structure is given. FIG. 3 shows the complexity of the structure for three degrees of freedom. The expansion to more than five to six degrees of freedom with the same or even a smaller diameter is very probably no longer able to be implemented.

SUMMARY OF INVENTION

The object of the invention is to specify an improved instrument system for minimally-invasive surgery.

The object is achieved by an instrument system in accordance with the independent claim. The instrument system comprises an endoscopic instrument which in its turn has a flexible support arm and a work head attached to the end of the support arm able to be introduced into a patient. The instrument system further comprises a trocar able to be placed in the body surface of a patient. This comprises a main body with a through-opening for the instrument. The main body is able to be fixed at a particular location relative to the patient or on said patient. The trocar also comprises a guide body. When the instrument is inserted into the trocar the guide body encloses a longitudinal section of the support arm with a guide channel, guiding it such that, at least in the area of the guide channel, a spatial direction of guidance of the support arm or of its longitudinal section is determined. The trocar also has an adjusting element which acts on the guide body such that this causes an explicit change in the relative position of the guiding direction to the main body.

To use the instrument system the trocar is initially placed on the patient as normal, i.e. its main body is generally laid onto the skin surface of the patient and is fixed locally there, e.g. by adhesive tape. The instrument, or its support arm with the work head at the front, is introduced through the through-opening into the trocar and through this into the patient until the work head comes to rest in the patient.

In this case the instrument is held at the opposite end of the support arm to the work head, e.g. is thus fixed in a robot arm as mentioned above. The support arm is flexible enough to be able to follow the movements of the trocar. In the area of the through-opening for example the support arm remains in an unchanged position. In the area of the guide body the support arm is moved. This leads to a deformation of the support arm per se. At least the longitudinal section of the support arm influenced by the guide body can thus accordingly be aligned in a desired guiding direction. The flexibility of the support arm in this case is as a rule also selected small enough for the work head also to move in a desired direction through the movement of the longitudinal section of the support arm. In other words the part of the support arm extending from the guide body to the work head has enough inherent stability to explicitly make possible a corresponding alignment of the work head through the guide body. The guiding direction thus describes an alignment of the support arm in a desired direction, which then as a rule corresponds roughly to the alignment of the work head. The end of the trocar remote from the main body forms the guide body for example and thus provides the maximum movement and the best option for guiding the work head.

In accordance with the invention it is thus proposed to relocate the drive concept of an instrument—at least partly—to the trocar. In other words the trocar carries out at least a rough positioning of the work head in the work space. Thus an orientation setting of an instrument tip, i.e. the work head, is also achieved. In other words, instead of a rigid trocar, a trocar equipped with a controllable movement action is proposed, which merely serves for rough positioning or steering of the instrument. The trocar thus deforms the instrument or its support arm respectively into a desired work space position, without in this case a transition or a boundary from the elastic to plastic deformation of the instrument shaft, i.e. of the support arm, being exceeded. The work head, i.e. the instrument tip, can thus be explicitly moved within a work space spanned by the possible movements of the trocar. For this movement no active inherent movability is necessary in the instrument itself, which is therefore able to be especially simple in its construction.

An axial shift of the instrument in the trocar brings a degree of freedom here at least controllable from outside the trocar for the instrument movement or movement of the work head. The same applies to a rotation of the support arm and thus of the work head around the central longitudinal axis of the instrument. Both movements can be operated in a simple manner from outside the patient by advancing and rotating the instrument.

What is thus proposed is a distribution of an overall drive concept to a rough positioning of the work head in the work space with the aid of the trocar and a fine positioning or orientation setting of the instrument tip through the movement of the instrument.

In a preferred embodiment a gap between the main body and an exit end of the guide body is able to be changed with the aid of an adjustment element. In other words the axial length of the trocar which extends within the patient, i.e. along an inserted instrument, is thus designed to be variable. The guide characteristic of the trocar can thus be used especially flexibly inside the patient. For example the guide body can be guided especially close to an organ to be treated by lengthening or shortening the trocar for a desired guiding direction, in order to let the instrument or the work head respectively only project minimally from the guide body and in order to thus be able to guide said instrument or head as exactly as possible.

In a further preferred embodiment the trocar contains a resetting device which acts on the guide body such that it brings said body into a basic position or resets it respectively. The resetting direction ensures in other words that, on resetting, the trocar always assumes a specific basic position, e.g. with the known distance and a known guiding direction for the instrument. In such cases the distance between main body and guide body and its guiding direction or relative position to the main body is known. In other words the trocar exit lying inside the patient can be moved back into a rest position or into initial state, after this has been previously moved in desired direction. An inserted instrument can thus likewise be bought into an initial position again. In particular resetting into the basic position is automatic, e.g. whenever no particular relative position is desired.

In a preferred variant of the above embodiment the resetting device includes a spring element bringing about the resetting. For example the main body is connected at one end of the trocar via a coil spring to the movable guide body at the other end of the trocar. In other words the trocar must always be taken out of the basic position and held there by applying a force against the spring element. If no adjusting force is acting on the guide body, said body aligns itself in a basic position in relation to its alignment and its distance from the main body. The basic position is predetermined by the relaxed position of the spring element.

In a further embodiment the instrument contains a control line running in the support arm, which is used for controlling an actuator of the support arm and/or of the work head. Thus further degrees of movement freedom on the support arm or work head can be realized by the actuators. An actuator is for example a joint in the support arm or an actuatable tool on the work head, such as a gripper or scissors.

For corresponding control lines to actuators there is thus considerably more space available than in such instruments which are moved solely by internal control lines, since the basic movement functionality in accordance with the invention is realized by the trocar and thus the entire internal space of the instrument is available for example for control lines. If there is space in the support arm for a number of control lines, a number of actuators can also be provided on the instrument itself.

The inventive distributed drive concept thus means that the number of cables to be guided through the instrument is reduced for the same functionality. The instrument can therefore assume a very small diameter. In addition the instrument remains inexpensive because of its low complexity, so that advantageously it can be designed as a disposable element.

In a preferred variant of this embodiment the control line is embodied to operate mechanically. For example the control line is a cable already explained above which is guided through the instrument or through its support arm respectively. Two or four cables are able, because of the distributed drive concept in this case however, to be integrated significantly more simply and unproblematically into an instrument than the twelve cables mentioned above. A functionality at the instrument tip is thus realized for example in the known manner by cable mechanisms.

In a preferred embodiment of the invention the adjustment element of the trocar is embodied to operate mechanically. Here too for example cables are conceivable, with the aid of which the guide body in the trocar can be operated or manipulated.

In a preferred variant of this embodiment the instrument system contains a drive which actuates one of the adjustment elements, especially that of the trocar. The drive in its turn can for example be operated by a computer control, so that ultimately a system-controlled change of the guidance direction or of a space between main body and guide body, i.e. a computer-controlled movement of the instrument in the patient, can be undertaken by the trocar.

BRIEF DESCRIPTION OF DRAWINGS

For a further description of the invention the reader is referred to the exemplary embodiments of the drawings, in which, in a schematic basic diagram in each case.

DETAILED DESCRIPTION OF INVENTION

Figure 1:
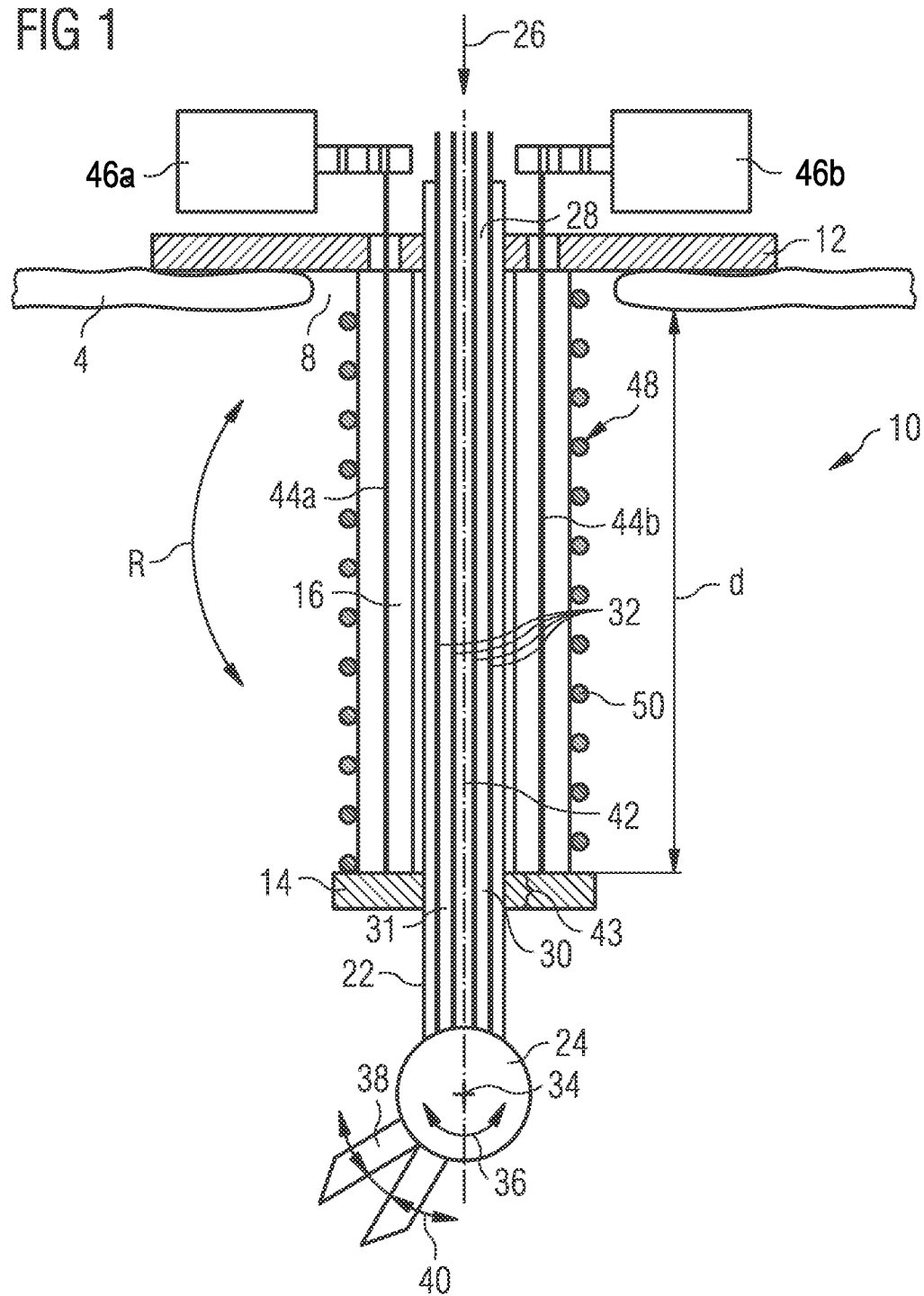
FIG. 1 shows an inventive instrument system in a basic position during use in a patient.

FIG. 1 shows a section of a patient, namely the surface of their body 4 in the form of the abdominal wall and its inside in the form of the abdominal cavity. An incision 8 is made operatively into the surface of the body 4, through which a trocar 10 is introduced into the patient. The trocar 10 has a main body 12 which is fixed locally on the patient, namely on their abdominal wall 4, e.g. with the aid of adhesive tapes not shown in the figure. The trocar 10 also has a guide body 14 which is connected via a flexible jacket 16 to the main body 12.

The trocar 10 is part of an instrument system, with the aid of which a medical procedure is to be performed on the patient. The instrument system also includes an endoscopic instrument 20 in the form of a laparoscope, which for its part contains a flexible support arm 22, attached to the end of which is a work head 24 able to be introduced into the patient.

At the beginning of the medical procedure at least the trocar 10 or the main body 12, as shown in FIG. 1, is fixed to the patient. Subsequently the instrument 20 is introduced in the direction of the arrow 26 into the trocar 10. For this purpose the main body 12 has a through-opening 28 and the guide body 14 has a guide channel 30. A number of control lines 32 in the form of cables run inside the instrument 20, which serve to operate the work head 24 and with which the work head 24 is able to be pivoted both around an axis 34 in the direction of the double arrow 36 and also an actuator 38 attached to the work head 24 in the form of scissors is able to be operated in the direction of the double arrow 40.

The guide channel 30 is embodied or acts in conjunction with the support arm 22 such that, in the area of the guide channel 30, it prespecifies a guiding direction 42 for the longitudinal section 43 of the support arm 22 inserted there. The guiding direction defines the spatial alignment of the support arm 22 at the position of the longitudinal section 43. Since the support arm 22 is not infinitely flexible, the spatial position of the work head 24 is thus also determined. In other words the support arm 22 emerges at an exit end 31 from the guide body 14 or the guide channel 30. The exit end 31 is at a distance d from the main body 12.

The trocar 10 also has adjustment elements 44a, b in the form of a cable, which is suitable for bringing about an explicit change of position of the guide body 14 in respect of the main body 12. In other words the relative location R between guide body 14 and main body 12 is determined. By changing the relative location R the direction of the guiding direction 42 is changed and thus the alignment of the support arm 22 and thus of the work head 24.

FIG. 1 shows the trocar in a basic position, i.e. with a specific predetermined relative location R.

Figure 2:
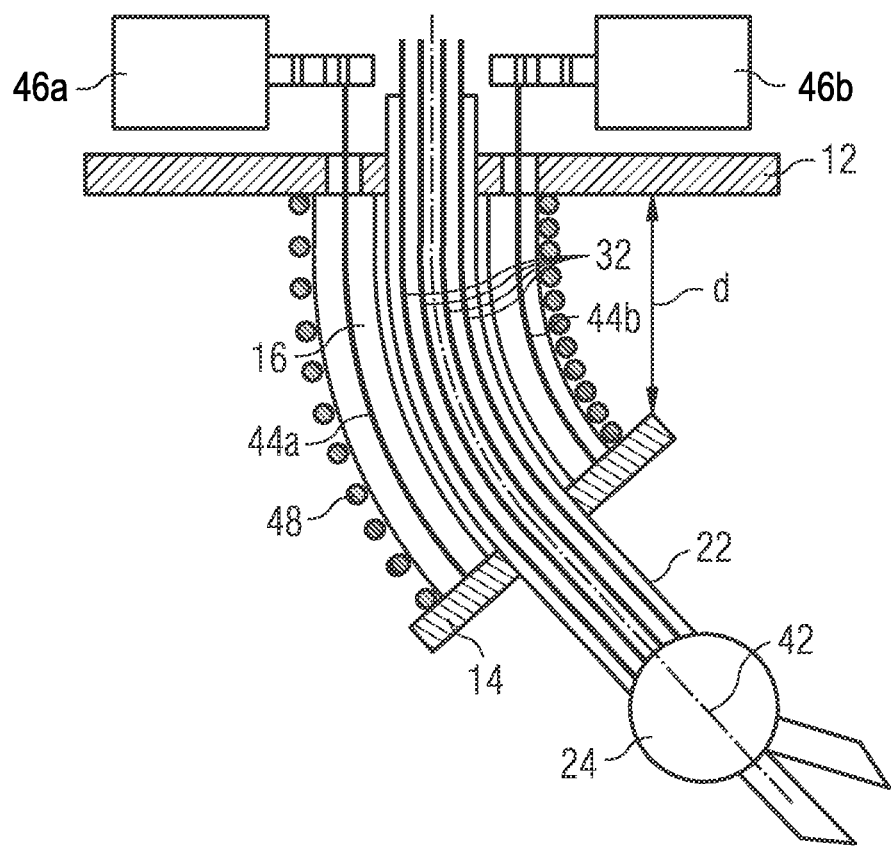
FIG. 2 shows the instrument system from FIG. 1 in a work position.
Figure 3:
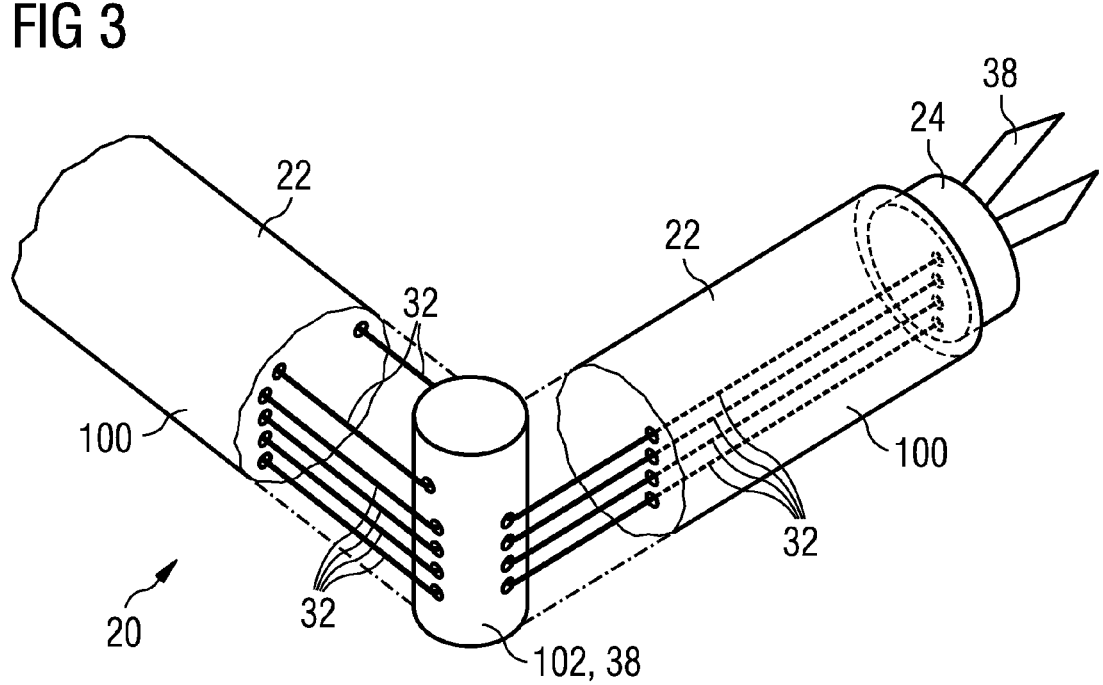
FIG. 3 shows an instrument with a complex cable mechanism.

FIG. 2 shows a situation in which the adjustment elements 44a, b have been actuated and thus the position of the guiding direction 42 has also been changed. The trocar is thus located in a work position in which the relative location R has been changed.

In the example both adjustment elements 44a, b have been moved, however the adjustment element 44b shortens more than the adjustment element 44a. The effect of this is that not only is the spatial position of the guiding direction 42 changed, but also the distance d between the guide body 14 and the main body 12 has lessened in relation to the basic position. Through this movability the instrument 20 is especially able to be maneuvered in relation to its work head 24 in a wide area inside the patient. To operate the adjustment elements 44a, b drives 46a, b respectively are provided, which are electrically controllable and thus can be used as part of a computer control for aligning the instrument 20 with the aid of the guide body 14.

The trocar 10 also includes a resetting device 48 in the form of a spring element 50, namely a coil spring connecting the main body 12 and guide body 14 and enclosing the jacket 16. In the basic position shown in FIG. 1 this is in the relaxed or powerless state. In the operating state of FIG. 2 the resetting device 48 is deformed. If, starting from the operating position, the adjusting elements 44a, b operating under tension are relieved again, the trocar 10 automatically, i.e. without external force effect through the resetting forces of the resetting device 48, moves back into the rest state shown in FIG. 1, i.e. the basic position.

The invention claimed is:

1. An instrument system, comprising:
an endoscopic instrument comprising a work head attached to one end of a flexible support arm to be introduced into a patient; and
a trocar to be placed in a surface of the patient's body comprising:
a main body to be fixed locally relative to the patient with a through-opening for the endoscopic instrument,
a guide body which, with the endoscopic instrument inserted into the patient, encloses a longitudinal section of the support arm with a guide channel guiding the guide body such that at least a spatial guidance direction of the support arm is defined in the longitudinal section,
a plurality of cables acting on the guide body causing an explicit change of a relative position of the guidance direction relative to the main body, and
a spring element connecting the main body to the guide body,
wherein the cables are actuated to locate the trocar to a work position,
wherein the cables are shortened differently with respect to each other when the cables are actuated,
wherein a distance between the main body and an exit end of the guide body and the spatial guidance direction of the support arm are changed in relation to a basic position of the trocar when the cables are actuated,
wherein the spring element is relaxed when the trocar is in the basic position, wherein the cables apply a force against the spring element when the cables are actuated, wherein the spring element is deformed when the trocar is held in the work position by applying a force against the spring element via the cables, wherein the trocar moves back from the work position to the basic position by relieving the force against the spring element via the cables, and wherein the spring element is located around the cables.

2. The instrument system as claimed in claim 1, wherein the endoscopic instrument comprises a control line running in the support arm controlling an actuator of the support arm and/or the work head.

3. The instrument system as claimed in claim 2, wherein the control line is adapted to operate mechanically.

4. The instrument system as claimed in claim 1, wherein the cable is adapted to operate mechanically.

5. The instrument system as claimed in claim 1, further comprising a plurality of drive members actuating the cables respectively.

6. The instrument system as claimed in claim 1, wherein the basic position is predetermined by a relaxed position of the spring element.

\* \* \* \* \*